United States Patent [19]

Imai

[11] Patent Number: 5,358,405
[45] Date of Patent: Oct. 25, 1994

[54] TOOTH FIXING MEMBER AND METHOD OF FIXING TEETH WITH THE MEMBER

[75] Inventor: Mototsugu Imai, Osaka, Japan

[73] Assignee: Daigen Sangyo Inc., Osaka, Japan

[21] Appl. No.: 19,989

[22] Filed: Feb. 17, 1993

Related U.S. Application Data

[63] Continuation of Ser. No. 894,052, Jun. 3, 1992, abandoned.

[30] Foreign Application Priority Data

Jun. 5, 1991 [JP] Japan ................ 3-162163

[51] Int. Cl.$^5$ .................. A61C 5/00; A61C 13/12; A61C 13/225; A61C 3/00
[52] U.S. Cl. .................. 433/215; 433/172; 433/18; 433/24
[58] Field of Search .............. 433/7, 18, 19, 20, 21, 433/24, 173, 176, 180, 181, 182, 215, 172

[56] References Cited

U.S. PATENT DOCUMENTS

| | | |
|---|---|---|
| 3,822,472 | 7/1974 | Garfinkel . |
| 4,256,456 | 3/1981 | Wallshein .................. 433/21 |
| 4,332,563 | 6/1982 | Weissman .................. 433/215 |
| 4,468,201 | 8/1984 | Fukuyo . |
| 4,735,571 | 4/1988 | Salvo .................. 433/215 |
| 5,011,404 | 4/1991 | Losi .................. 433/19 |
| 5,044,947 | 9/1991 | Sachdeva et al. .................. 433/18 X |

FOREIGN PATENT DOCUMENTS

| | | |
|---|---|---|
| 0309604A1 | 4/1989 | European Pat. Off. . |
| 49-50790 | 5/1974 | Japan . |
| 58-44047 | 3/1983 | Japan . |

*Primary Examiner*—Paul J. Hirsch
*Assistant Examiner*—Nicholas D. Lucchesi
*Attorney, Agent, or Firm*—Darby & Darby

[57] ABSTRACT

A tooth-fixing member of a shape memory alloy including two pairs of fixing fingers formed on both sides of a band base for engaging teeth, the pair of fixing fingers being processed to open in parent phase and close in martensite phase. Tooth fixing procedure includes the steps of: forming a cavity in each of plural target teeth; inserting each pair of fixing fingers of the tooth-fixing member in martensite phase into the cavity; and heating the tooth-fixing member to the parent phase to open the fixing fingers so as to fix the teeth together. The tooth-fixing member applicable to various dental treatments, which include: fixation of teeth which are loose due to periodontal diseases like pyorrhea alveolaris; fixation of teeth to ensure a space for a tooth to erupt; fixation of a tooth which is extruding abnormally; fixation of a transplanted tooth; and correction of slanting teeth.

21 Claims, 9 Drawing Sheets

TOOTH FIXING MEMBER AND METHOD OF FIXING TEETH WITH THE MEMBER

This is a continuation, of application Ser. No. 07/894,052, filed Jun. 3, 1992, now abandoned.

BACKGROUND OF THE INVENTION

1. Field of the Invention

The present invention relates to a tooth-fixing member used for fixing teeth which are loose due to periodontal diseases like pyorrhea alveolaris, and also to a method of fixing teeth with the fixing member.

2. Description of Related Art

As the periodontal tissue is successively damaged from the circumference of gingiva and alveolar bone gradually recedes in the course of periodontitis, teeth in the lesion of periodontitis become loose; this is a typical symptom of pyorrhea alveolaris. There are mainly two treatment procedures for teeth in pyorrhea alveolaris: extraction of a tooth which is extremely loose and of no use; and fixation of a tooth, which is loose but has some chance to survive, to an adjacent tooth with no or only slight looseness.

Fixation of a loose tooth to an adjacent tooth is generally implemented with metal wire. In concrete terms, target teeth, that is, a loose tooth, and its adjacent tooth, are tied with metal wire having sufficient elasticity and are then exposed to loading due to bending or tension of the metal wire so as to be securely fixed.

The method mentioned above, however, has some drawbacks; fastening target teeth with metal wire is both labor and time consuming; loading applied to the teeth gives a patient persistent pain and uncomfortable feeling; and the metal wire is undesirably seen whenever the patient opens the mouth.

Some methods of correcting the dental arch with shape memory alloy have been proposed; for example, Japanese Patent Laid-Open No. 49-50790 and No. 58-44047. An example of such method is briefly explained. An orthodontic member of shape memory alloy wire is processed through heat treatment so as to have a desirable shape to give the anatomically favorable dental arch in parent phase. The processed orthodontic member is fit on the dental arch of a patient at relatively low temperatures and is then heated to regain the original shape, thereby correcting the dental arch by taking advantage of its elastic force. While there are several disclosures regarding such orthodontic members of shape memory alloy, application of shape alloy metal to a tooth-fixing member has not yet been proposed.

SUMMARY OF THE INVENTION

The general object of the invention is thus to provide tooth-fixing member for readily fixing target teeth without any specific techniques or skills, and also a method of fixing teeth with the fixing member.

A specific object of the invention is to provide a tooth-fixing member with sufficient resistance against biting force and rotational stress, and also a method of fixing teeth with the fixing member.

Another specific object of the invention is to provide a tooth-fixing member which does not give a patient persistent pain or discomfort and attains favorable appearance, and also a method of fixing teeth with the fixing member.

The above and other related objects are realized by a tooth-fixing member composed of a shape memory alloy, including a band base; and two pairs of fixing fingers each pair integrally projecting from the respective end of the band base for engaging a tooth, the pair of fixing fingers being processed to open in parent phase and close in martensite phase.

Another feature of the invention is a method of fixing teeth, including the steps of: forming a cavity going through plural target teeth adjacent to each other; inserting the tooth-fixing member in martensite phase into the cavity; and heating the tooth-fixing member to open the fixing fingers, that is, to restore the original shape in parent state, and fixing the plural teeth together.

In another application of the method, only one pair of fixing fingers of the tooth-fixing member is inserted into a cavity formed in just one tooth while the other pair being brought into contact with the other tooth having no cavity.

The tooth-fixing member of the invention is applicable to various dental treatments, which include: fixation of teeth which are loose due to periodontal diseases like pyorrhea alveolaris; fixation of teeth to ensure a space for a tooth to erupt; fixation of a first molar as an infant distal shoe; fixation of a tooth which is extruding abnormally; fixation of a transplanted tooth; traction of a tooth which does not normally erupt; reinforcement of a damaged denture; and correction of a slanting tooth.

The above and further objects and features of the invention will more fully be apparent from the following detailed description with accompanying drawings.

BRIEF DESCRIPTION OF THE DRAWINGS

FIGS. 1 (*a*) and 1 (*b*) are plan views showing a tooth-fixing member embodying the invention;

FIGS. 2 (*a*) through 2 (*e*) are plan views illustrating a process of tooth fixing;

FIGS. 3(*a*) through 3(*e*) are cross sectional views illustrating the process of tooth fixing corresponding to Figs. 2 (*a*) through 2 (*e*);

DESCRIPTION OF THE PREFERRED EMBODIMENTS

The invention is described more concretely according to preferred embodiments thereof with the accompanying drawings.

Figure 1A:
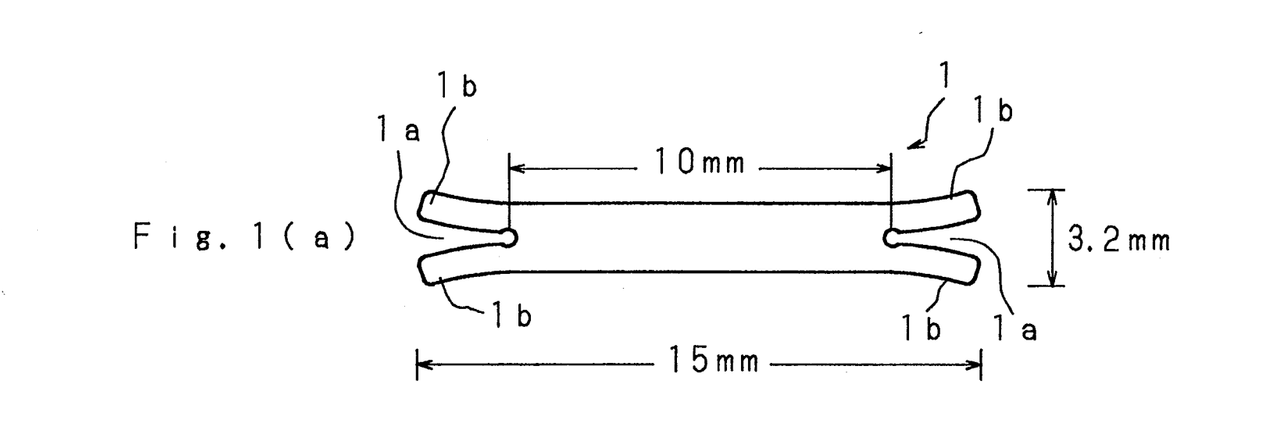
Figure 1B:
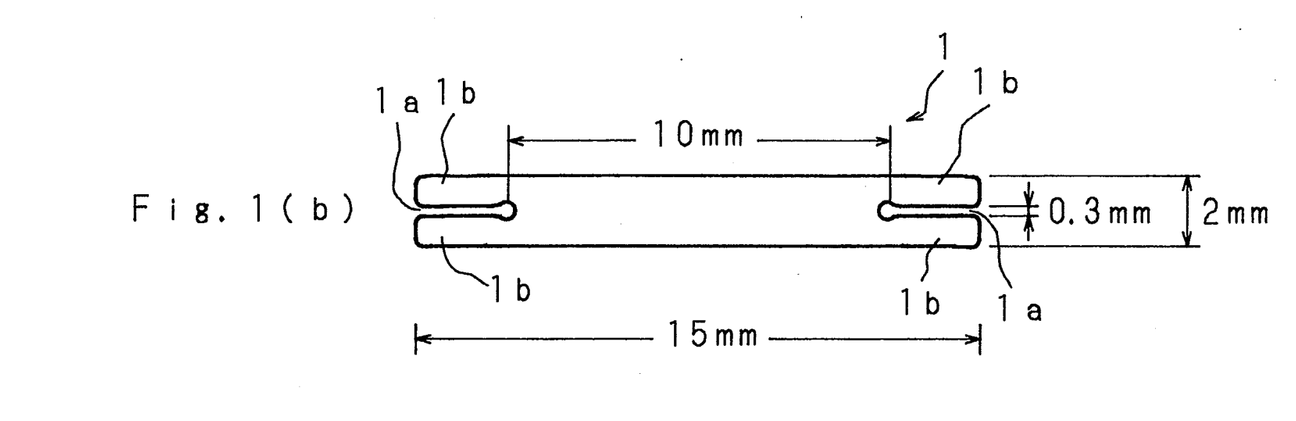

FIGS. 1 (*a*) and 1 (*b*) are plan views showing an embodiment of the invention, that is, a tooth-fixing member 1 composed of a Ni—Ti (nickel—titanium) shape memory alloy. Fig. 1 (*a*) shows the tooth-fixing member 1 processed at a high temperature for shape memory effects, that is, in parent phase (austenitc phase), and FIG. 1 (*b*) shows the tooth-fixing member 1 cooled after the shape memory process, that is, in martensite phase.

The tooth-fixing member 1 in martensite phase is typically a 15 mm long, 2 mm wide, and 1 mm thick band having cuts 1a, 1a (width: 0.3 mm, length: 2.5 mm) on both longitudinal ends. Each cut 1a, which is located in the middle of the width and in the longitudinal direction from each end of the band, forms a pair of fixing fingers 1b, 1b. The foot of each fixing finger 1b is chamfered. Each pair of fixing fingers 1b, 1b of the tooth-fixing member 1 are open in the direction of the width about the cut 1a in parent phase. The shape of the tooth-fixing member 1 in parent phase is identical with that in martensite phase except that the fixing fingers 1b, 1b are open.

Ni—Ti alloy is a superlattice alloy with thermo-elastic martensitic transformation, which is characterized by a small hysteresis in normal and reverse transformation between parent and martensite phases. This transformation is also crystallographically reversible; that is, both the crystal structure and orientation are restored to the original state through reverse transformation. As the alloy is cooled after the shape memory treatment, martensitic transformation starts at a martensite starting temperature Ms and is completed at a martensite finishing temperature Mf. When the Ni—Ti alloy in martensite phase is heated, on the contrary, reverse transformation starts at a reverse transformation starting temperature As and is completed at a reverse transformation finishing temperature Af. Heating over the temperature Af is required for perfect restoration of the original shape. Thermo-elastic martensitic transformation completely restores the original shape of the crystal with atomic combination unchanged in parent phase, because of its reversible characteristic.

Manufacture of the tooth-fixing member 1 and thermal characteristics of transformation are now described. Nickel and titanium material molten in vacuum at a high frequency is cast in a copper mold, polished on the surface, and thermally treated at 450° C. for one hour to give the original shape shown in FIG. 1 (a) through the shape memory process. The tooth-fixing member 1 thus manufactured has the reverse transformation starting temperature As at approximately 20° C. and the finishing temperature Af a approximately 40° C. The length and shape of the tooth-fixing member 1 are determined corresponding to the distance between plural target teeth and dental arch of the teeth.

Figure 2A:
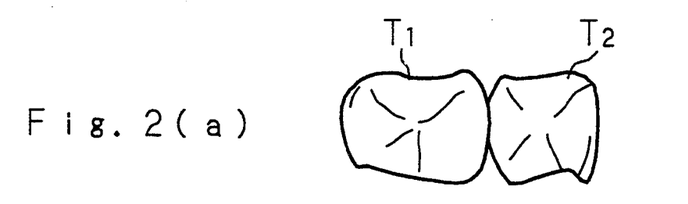
Figure 2B:
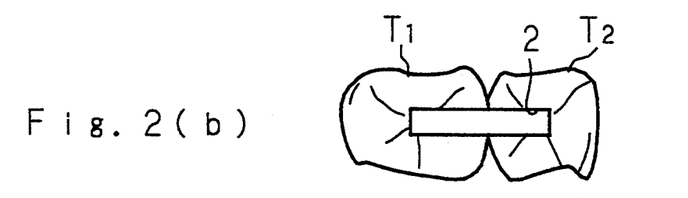
Figure 2C:
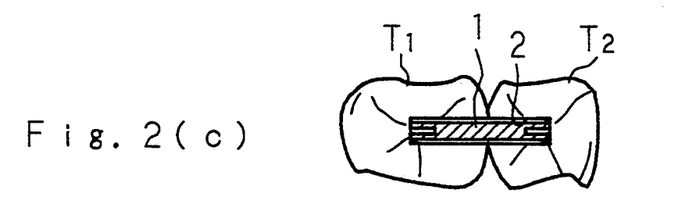
Figure 2D:
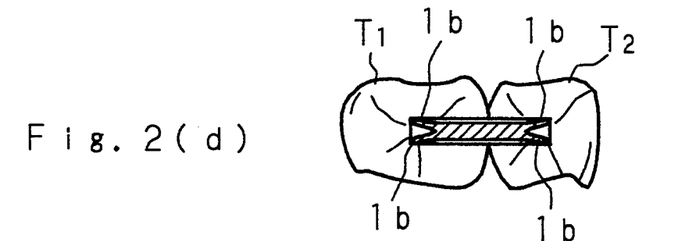
Figure 2E:
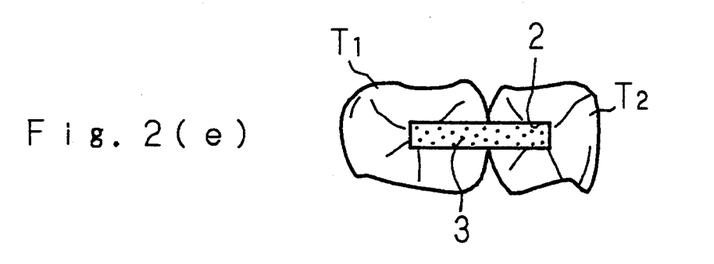
Figure 3A:
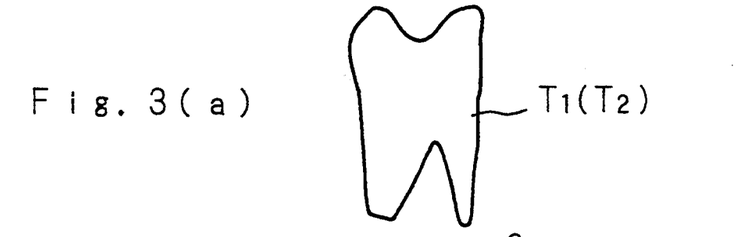
Figure 3B:
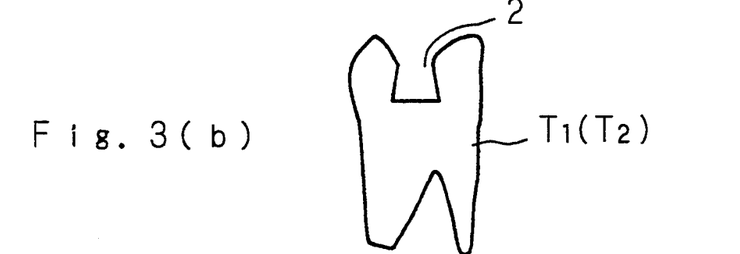
Figure 3C:
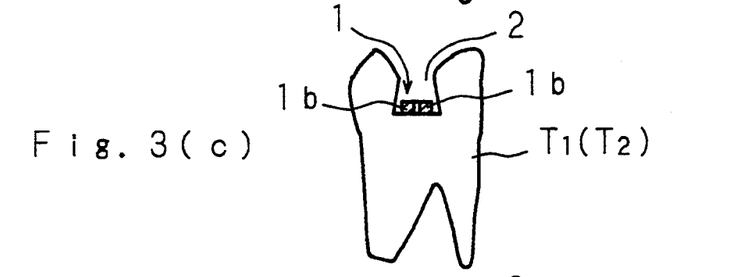
Figure 3D:
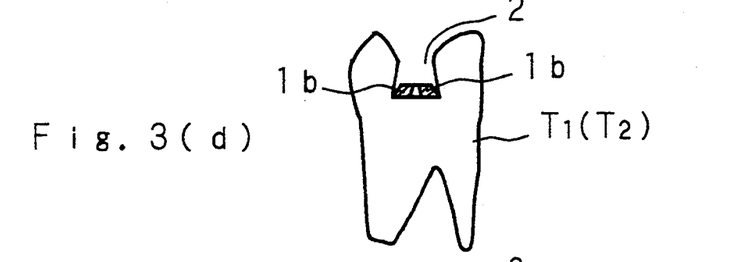
Figure 3E:
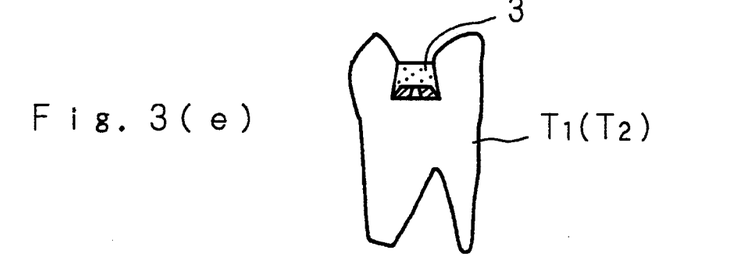

The process of fixing plural teeth adjacent to each other with the tooth-fixing member 1 is described briefly. FIGS. 2 (a) through 2 (e) and FIGS. 3 (a) through 3 (e) are plan views and cross sectional views explaining the process, respectively. In FIG. 2(a) and FIG. 3(a), a tooth T1 is extremely loose due to pyorrhea alveolaris, and an adjacent tooth T2 has substantially no or only a slight looseness. The distance between the target teeth T1 and T2 and the curvature of the dental arch are measured, and a tooth-fixing member 1 is prepared based on the data. A cavity 2 going through the teeth T1 and T2 is formed to have a narrower width on the crown side than on the dental root side ( see FIG. 2(b) and FIG. 3(b)). The tooth-fixing member 1 in martensite phase as shown in FIG. 1 (b) is inserted into the cavity 2 (see FIG. 2 (c) and FIG. 3 (c) ). Heat is,applied to raise the temperature of the tooth-fixing member 1 to the value Af or higher. At the temperature Af, the tooth-fixing member 1 is restored to the original state shown in FIG. 1(a), and the two pairs of fixing fingers 1b, 1b on both sides of the member 1 open to engage with the taper surface of the cavity 2. Namely, the tooth-fixing member 1 mechanically connects with the teeth T1 and T2 (see FIG. 2(d) and FIG. 3(d)). After checking the mechanical connection, clearance of the cavity 2 is filled with resin 3, which reinforces the connection between the teeth T1 and T2 ( see FIG. 2(e) and FIG. 3(e)).

The tooth-fixing member 1 can be used in the same manner to fix three or more adjacent teeth or two teeth with a space therein.

In the application described above, the tooth-fixing member 1 is used to fix a loose tooth due to periodontal diseases such as pyorrhea alveolaris. The tooth-fixing member 1 of the embodiment is also applicable to other treatment procedures, which are explained hereinafter.

Figure 4:
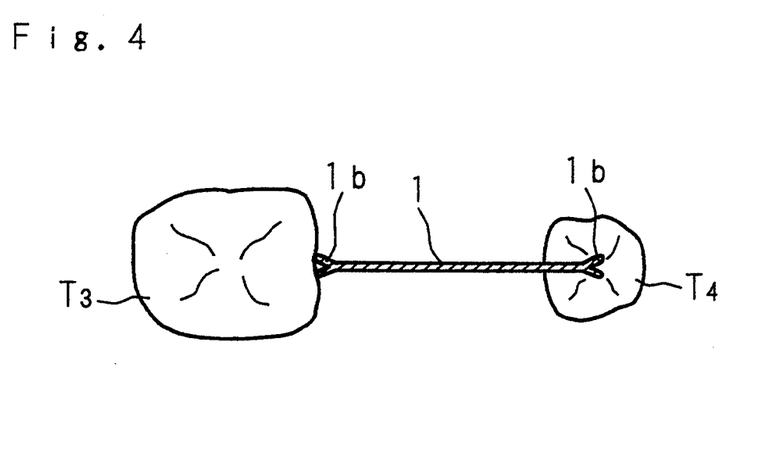
FIG. 4 is a schematic view showing an application of the tooth-fixing member of the embodiment.

FIG. 4 is a schematic view showing the tooth-fixing member 1 used for ensuring a predetermined space. Here, as shown, a new molar is to erupt between a molar T3 which has already erupted and a remaining deciduous molar T4. One pair of fixing fingers of the tooth-fixing member 1 are inserted into a cavity formed in the deciduous molar T4 while the other end thereof is brought into contact with the molar T3. A space is thereby kept between the two teeth T3 and T4 for smooth eruption of a new molar.

Figure 5:
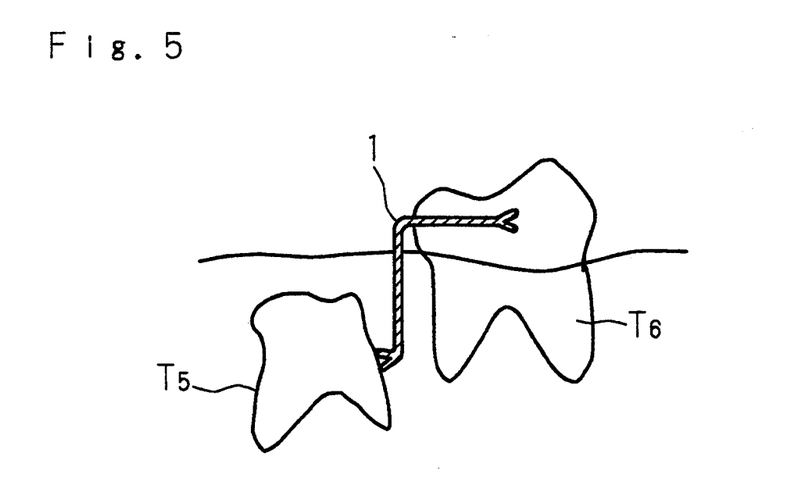
FIG. 5 is a schematic view showing another application of the tooth-fixing member of the embodiment.

FIG. 5 is another application of the tooth-fixing member 1 as a distal shoe. When a second deciduous molar comes out before a first molar erupts, mesial dislocation of the first molar might occur. One pair of fixing fingers of the tooth-fixing member 1 are inserted into a cavity formed in a remaining first deciduous molar T6 while the other end thereof is brought into contact with a first molar T5, thus preventing the mesial dislocation of the first molar T5 and promoting smooth eruption of the first molar T5.

Figure 6:
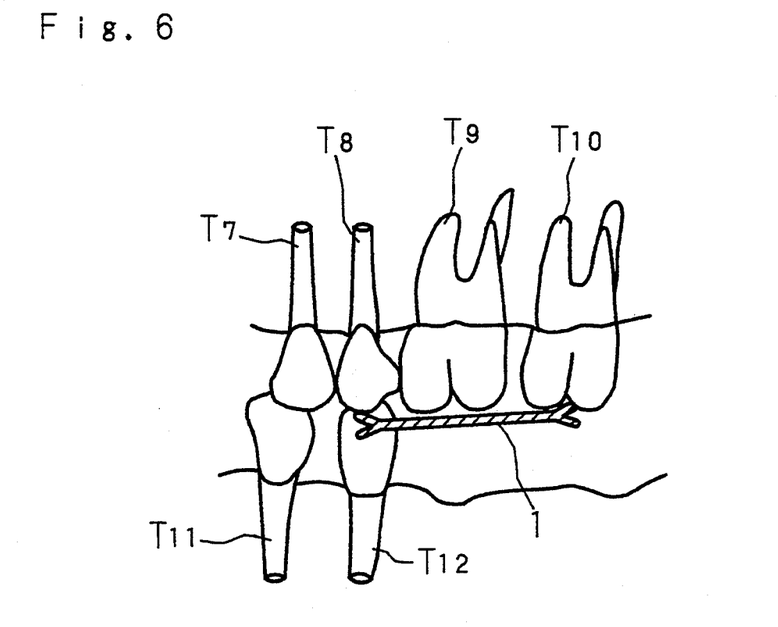
FIG. 6 is a schematic view showing a further application of the tooth-fixing member- of the embodiment.

FIG. 6 is a schematic view showing the tooth-fixing member 1 applied to a tooth which may abnormally extrude. In the drawing, teeth T7 through T10 are on the maxilla side and T11 and T12 on the mandible side. The teeth T9 and T10 on the maxilla side do not have occlusal mates on the mandible side and may abnormally extrude downward from the occlusal face. In such a case, one pair of fixing fingers of the tooth-fixing member 1 are inserted into a cavity formed in the tooth T12 on the mandible side while the other end thereof is brought into contact with the tooth T10, thus preventing abnormal extrusion of the teeth T9 and T10.

Figure 7:
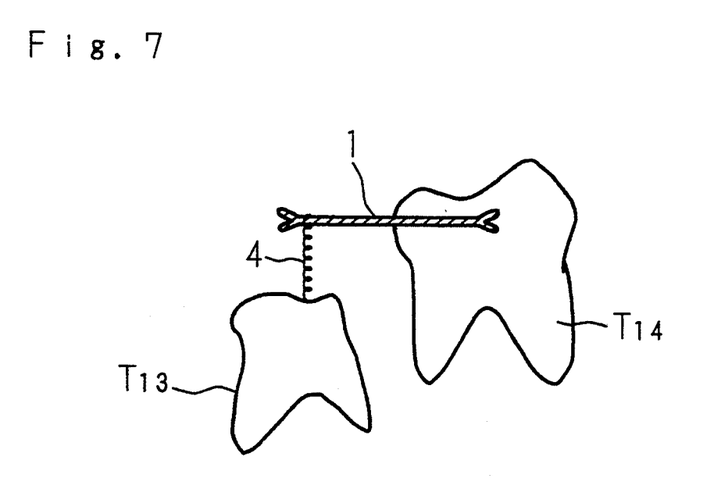
FIG. 7 is a schematic view showing still another application of the tooth-fixing member of the embodiment.

The tooth-fixing member 1 of the embodiment is also applicable to fixation of a transplanted tooth with a natural tooth adjacent thereto, FIG, 7 is a schematic view showing the tooth-fixing member 1 applied to a tooth which does not normally erupt. One pair of fixing fingers of the tooth-fixing member 1 are inserted into a cavity formed in a normal tooth T14 while the other end thereof is placed above a tooth T13 which does not normally erupt. The non-inserted end of the tooth-fixing member 1 is bound to the abnormal tooth T13 with a metal wire or plastic thread 4 for promoting the eruption of the tooth T13.

Figure 8:
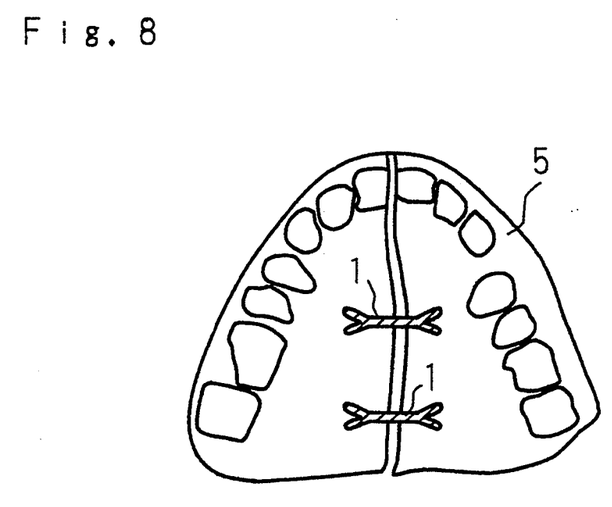
FIG. 8 is a schematic view showing a further application of the tooth-fixing member of the embodiment.

FIG, 8 is a schematic view showing the tooth-fixing member 1 applied to a denture 5. A damage or broken portion of the denture 5 is reinforced with the tooth-fixing member 1.

Figure 9:
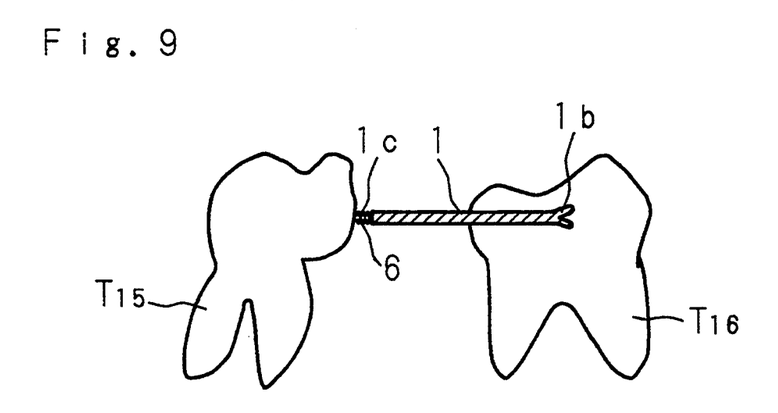
FIG. 9 is a schematic view showing another application of the tooth- fixing member of the embodiment.

FIG. 9 is a schematic view showing the tooth-fixing member 1 of the embodiment applied to correction of a slanting tooth. The tooth-fixing member 1 has a pair of fixing fingers 1b, 1b on one end and a projection 1c with a coil spring 6 on the other end. The pair of fixing fingers 1b, 1b are inserted into a cavity formed on a normal tooth T16, and the projection 1c is brought into contact with a slanting tooth T15. Restoring force of the shape memory alloy, in cooperation with elastic force of the coil spring 6, corrects the slanting tooth T15. Elastic rubber may be substituted for the coil spring 6.

As this invention may be embodied in several forms without departing from the spirit, of essential characteristics thereof, the present embodiment is therefore illustrative and not restrictive. The scope of the invention is defined by the appended claims rather than by the description preceding them, and all changes that fall within metes and bounds of the claims or equivalence of such metes and bounds thereof are therefore intended to be embraced by the claims.

What is claimed is:

1. A tooth-fixing member comprising: a band base having a longitudinal axis and a respective pair of integral fixing fingers projecting in opposite directions generally along the longitudinal axis from each end of the band base for engaging a tooth, at least said fixing fingers being of a shape memory alloy which transforms its shape between a parent phase and a martensite phase the pairs of fixing fingers being formed to open in parent phase and close in martensite phase.

2. A tooth-fixing member in accordance with claim 1, wherein the shape memory alloy is a nickel-titanium alloy.

3. A tooth-fixing member in accordance with claim 2, wherein the shape memory alloy starts reverse transformation at approximately 20° C. and completes the reverse transformation at approximately 40° C.

4. A method of fixing a tooth with the tooth-fixing member according to claim 1, comprising the steps of:
    forming a cavity in each of a loose tooth and a non-loose tooth;
    inserting the tooth-fixing member in martensite phase into the cavity of each tooth; and
    heating the tooth-fixing member to open at least one of the pairs of fixing fingers so as to fix the loose tooth.

5. A method of fixing a tooth in accordance with claim 4, further comprising the step of: filling a cavity with resin after heating the tooth-fixing member to open said at least one of the pairs of fixing fingers.

6. The method of claim 4 wherein both pair of fingers open upon heating of the member.

7. The method of claim 4 wherein said at least one pair of fingers open outwardly substantially in the same plane as said band base.

8. The method of claim 7 wherein both pairs of fingers open outwardly substantially in the same plane as the band base.

9. A method of fixing teeth adjacent to a non-erupting tooth with the tooth-fixing member according to claim 1 so as to ensure a space for the non- erupting tooth to erupt between two adjacent teeth, comprising the steps of:
    forming a cavity in one adjacent tooth;
    inserting a pair of fixing fingers of the tooth-fixing member in martensite phase into the cavity, and bringing the other pair into contact with an other adjacent tooth; and
    heating the tooth-fixing member to open the fixing fingers of each pair so as to fix the two adjacent teeth.

10. A method of fixing teeth in accordance with claim 9, wherein one adjacent tooth is a deciduous tooth and the other adjacent tooth is a permanent tooth.

11. The method of claim 9 wherein upon heating of the member the fingers of at least one pair extend sidewise from the plane of said band base.

12. The method of claim 11 wherein upon heating of the member the fingers of both pair of fingers extend sidewise from the plane of said band base.

13. A method of fixing teeth using the tooth-fixing member according to claim 1 as a distal shoe, comprising the steps of:
    forming a cavity in a remaining deciduous molar;
    inserting a pair of fixing fingers of the tooth-fixing member in martensite phase into the cavity, and bringing the other pair of fingers into contact with a molar to erupt; and
    heating the tooth-fixing member to open at least one of the pairs of fixing fingers so as to limit horizontal movement of the molar to erupt.

14. A method of fixing a tooth with the tooth-fixing member according to claim 1 so as to prevent abnormal extrusion of a tooth, which does not have an occlusal mate, from the occlusal face thereof, comprising the steps of:
    forming a cavity in a tooth which has an occlusal mate;
    inserting a pair of fixing fingers of the tooth-fixing member in martensite phase into the cavity, and bringing the other pair of fingers into contact with the tooth without the occlusal mate; and
    heating the tooth-fixing member to open at least one of the pairs of fixing fingers so as to fix the tooth without the occlusal mate.

15. A method of promoting eruption of a tooth which does not normally erupt with the tooth-fixing member according to claim 1, comprising the steps of:
    forming a cavity in a tooth which has erupted;
    inserting a pair of fixing fingers of the tooth-fixing member in martensite phase into the cavity, and placing the other pair of fingers above the tooth which does not normally erupt;
    connecting the other pair of fixing fingers of the tooth-fixing member to the tooth which does not normally erupt with a metal wire; and
    heating the tooth-fixing member to open the pair of fixing fingers in the cavity.

16. A tooth-fixing member as in claim 1 wherein in the parent phase the fingers open outwardly substantially in the same plane as said band base.

17. A tooth-fixing member as in claim 1 wherein in the parent phase the fingers open to extend sideways of the plane of the band base.

18. A method of correcting a slanting tooth comprising:
    providing a tooth-fixing member having a band base, a pair of fixing fingers of a shape memory alloy integrally projecting from one end of the band base, and a projection extending from the other end of the band base, the pair of fixing fingers being formed to open in parent phase and close in martensite phase;
    forming a cavity in a non-slanting tooth;
    inserting the pair of fixing fingers of the tooth-fixing member in martensite phase into the cavity, and bringing the projection thereof into contact with the slanting tooth via an elastic member; and
    heating the tooth-fixing member to the fixing fingers.

19. A method in accordance with claim 18, wherein the projection extending from the other end is an elastic member.

20. A method as in claim 19 wherein the elastic member is a coil spring or a section of elastic rubber.

21. The method of claim 20 wherein there is a pair of said fingers at each end of the band base.

* * * * *